(12) United States Patent
Berthou et al.

(10) Patent No.: US 6,517,525 B1
(45) Date of Patent: Feb. 11, 2003

(54) ABSORBENT PRODUCT

(75) Inventors: Thomas Berthou, Gothenburg (SE); Marie Utas Hansson, Lindome (SE); Anne Guri Andresen, Vastra Frolunda (SE); Richard Fredriksson, Gothenburg (SE); Eje Osterdahl, Vastra Frolunda (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/221,847

(22) Filed: Dec. 29, 1998

(30) Foreign Application Priority Data

Dec. 29, 1997 (SE) ................................................ 9704893

(51) Int. Cl.⁷ ............................ A61F 13/15; A61F 13/20
(52) U.S. Cl. ......................... 604/385.101; 604/385.01; 604/387
(58) Field of Search ............................... 604/365, 366, 604/379, 380, 385.01, 385.101, 385.201, 387

(56) References Cited

U.S. PATENT DOCUMENTS

| | | | | |
|---|---|---|---|---|
| 3,343,543 A | * | 9/1967 | Glassman | 604/386 |
| 3,411,504 A | * | 11/1968 | Glassman | 604/386 |
| 3,575,174 A | | 4/1971 | Mogor | |
| 3,805,790 A | * | 4/1974 | Kaczmarzyk et al. | 604/387 |
| 4,059,114 A | * | 11/1977 | Richards | 604/366 |
| 4,631,062 A | * | 12/1986 | Lassen et al. | 604/387 |
| 4,655,759 A | | 4/1987 | Romans-Hess et al. | |
| 4,752,349 A | * | 6/1988 | Gebel | 604/380 |
| 5,300,055 A | * | 4/1994 | Buell | 604/385.23 |
| 5,514,104 A | * | 5/1996 | Cole et al. | 604/386 |
| 5,591,150 A | * | 1/1997 | Olsen et al. | 604/386 |
| 5,688,259 A | * | 11/1997 | Osburn, III et al. | 604/386 |
| 5,891,118 A | * | 4/1999 | Toyoshima et al. | 604/380 |

FOREIGN PATENT DOCUMENTS

| | | |
|---|---|---|
| EP | 0 304 957 | 3/1989 |
| EP | 0 621 082 | 10/1994 |
| SE | 463 746 | 1/1991 |
| WO | 95/07674 | 3/1995 |

\* cited by examiner

*Primary Examiner*—Aaron J. Lewis
*Assistant Examiner*—K. M. Reichle
(74) *Attorney, Agent, or Firm*—Young & Thompson

(57) ABSTRACT

An absorbent product, such as a sanitary napkin, an incontinence protector or a panty liner. The product has an essentially elongated shape with a longitudinal direction and a transverse direction. The product has two long sides, two short sides, two end parts, a center part situated between the end parts and an absorption body. The product in the longitudinal direction of the product has elongated, curved compressions which have a bending radius of 300–450 mm, preferably 320–360 mm.

12 Claims, 2 Drawing Sheets

ABSORBENT PRODUCT

BACKGROUND OF THE INVENTION

1. Field of the Invention

The invention relates to an absorbent product such as a sanitary towel, an incontinence protector or a panty protector, which product has an essentially elongated shape with two long sides, two short sides, two end parts and a center part between the end parts having an absorption body. The product has elongated, curved compressions in the longitudinal direction of the product.

2. Description of the Related Art

Conventional absorbent products such as sanitary napkins, panty liners and protectors for mildly incontinent women normally have a planar, essentially rectangular shape with two long sides and two short sides. A planar shape has advantages, first and foremost because a product with a planar shape is easy to pack and distribute. However, a planar shaped absorbent product corresponds badly with the human anatomy. An absorbent product in the longitudinal direction can be roughly divided into a center part and two end parts. One of the end parts is intended to fit in the groin part of the user and the other end part is intended to fit in against the buttocks of the user. The center part should fit against the genitals in the crotch of the user and should initially receive the menstrual fluid or urine which is eliminated from the body of the user. The fit against the body is important in order to prevent leakage past the product.

Considering the different parts of the body which the parts of the product should fit against it is advantageous that the product has, or during use takes up, a bowl shape in the longitudinal direction. To shape a product so that it has a bowl shape in the longitudinal direction, EP 155 515 describes the use of, for example, elastic threads in the long sides of the product.

An alternative to preforming a product is to manufacture a product which is shaped during use. This can be achieved for example through compression lines arranged in the product. Such a product is shown in U.S. Pat. No. 4,655,759. This solution has the advantage that the product is flat in the packaging. A further advantage with compression lines is that an absorbent product is normally rather soft and pliable and can nevertheless be deformed during use when it is subjected to forces from the thighs and abdomen of the user. A controlled deformation is better than the random creases, diagonally or straight across the product, which spontaneously can occur in a product during the compression between the thighs of the user and which can lead to leakage.

A problem with the above-mentioned product comprising compressions is that they solely are adapted to be effective as leakage barriers, that is to say to prevent fluid from flowing over the longitudinal side edges of the product. No adaptation to the anatomy of the user has been made.

BRIEF SUMMARY OF THE INVENTION

The object of the invention is to remedy the above-mentioned problem and produce an absorbent product which adapts itself well to the body and which product is leakproof.

A product of the type mentioned in the introduction with which the problems associated with earlier known products are substantially avoided is characterized by compressions having a bending radius of 300–450 mm, preferably 320–360 mm.

According to one embodiment of the invention the product has longitudinally a center line around which two curved compressions are arranged so that the end parts of the curved compressions are at a greater distance from the center line than the middle parts of the compressions. The distance between the compressions is 25–35 mm, preferably the distance is 27.5–32.5 mm. The distance between the compressions is the shortest distance between the compressions measured in the transverse direction of the product.

According to yet another embodiment of the invention, the minimum distance between a compression and the nearest adjacent long side of the product is 5–20 mm, preferably the distance is 10–15 mm.

According to a further embodiment of the invention the length of the compressions are at least 50% of the length of the absorption body. According to one embodiment of the invention the compressions are 50–75% of the length of the absorption body. Alternatively the compressions are 60–85% of the length of the absorption body. The invention can be further characterized in that the compressions are joined to form a continuous compression running around the product.

Through the present invention the above-mentioned problems with bad fitting and leakage over the side edges of the products are solved. This is achieved through the compressions having a bending radius of 300–450 mm. With a bending radius of 300–450 mm a good leakage barrier is obtained at the same time as a good fit to the body is obtained. The length of the absorbent product is decisive as to how large the bending radius could be. In order to obtain an evenly controlled deformation the bending radius should increase when the length of the product increases. Because larger, and therefore longer products, are used with larger menstrual flows, it is also important for the function of the compressions as leakage barriers that the bending radius increases with increasing length of the product. The most advantageous bending radius from a body fitting point of view is however 320–360 mm.

In the case where the length of the product is 240 mm the bending radius from the compression is suitably 320–360 mm, preferably 340 mm. When the length of the product is 270 mm the bending radius for the compressions is suitably 400–450 mm, preferably 450 mm.

Because the center part of an absorbent product is the part which initially receives the considerably largest amount of menstrual fluid or urine, it is desirable that the center part has a large amount of absorption material. An easy way of producing this is to make the product wider in the center part than at the end parts. This would however be disadvantageous from the comfort and attachment point of view. Because the narrowest passage between the legs of the user corresponds to a large degree with the region where the body fluid is emitted, the product with a wider central part, which would be advantageous from the absorption point of view, will move itself forward when the user walks. From an attachment point of view it is consequently advantageous to have a narrower central part than end parts, that is to say an absorbent product which has the shape of an hourglass. The narrowest place between the user's legs is where the group of muscles passes which have its origins on the inside of the base of the pelvis and its attachment along the thigh. This group of muscles consists of the muscles Adductor Bre'vis, Adductor Lo'ngus, Gra'cilis and Adductor Ma'gnus.

Measurements have indicated that the distance in the crotch region of the user between these Adductor muscle groups on the right and left side is surprisingly similar for all people and lies around 30 mm. Fat naturally influences the width between the thighs but the width between the muscle groups in the crotch region is the same and it is this width which makes the user of a product experience chafing. The fat tissue lies on the outside of the muscles but does not contribute to the possible feeling of discomfort. If the product is constructed in an extremely stiff material the width of the center part therefore, at least in the region which passes between the muscle groups of each leg, should not be greater than 35 mm. The center part is the longitudinal center part, that is to say the part of the product which in the longitudinal direction of the product lies between the end parts of the product. The distance between the muscles of each leg is surprisingly similar for different individuals and is the distance which determines the comfort of the user. Certain people are more plump than others but the comfort is determined by the width of the product of the part which is to fit between the above-mentioned groups of muscles not being greater than the distance between these muscles. Fat tissue yields.

How wide a product can be is naturally also determined by the stiffness of the product. A soft product creases and wrinkles and does not act negatively on the comfort even if the width of the center part is greater than the distance between the muscle groups. An uncontrolled wrinkling however forms channels in the product in which the fluid can be transported towards the edges of the product and over them. Leakage occurs. Through arranging compression lines in the product a controlled deformation is obtained during compression between the thighs of the user. With the bending radia of the compressions which are mentioned according to the invention the product is deformed in a controlled way so that a good fit against the thighs of the user is obtained. At the same time the product takes up a more hourglass appearance and improved attachment is obtained. The product does not move forward when the user walks.

Preferably the absorbent product according to the invention has two longitudinal compressions arranged around a longitudinal center line of the product so that the outer parts of the curved compressions are at a larger distance from the center line than the center parts of the compressions. A longitudinal center line of the product is a line arranged in the longitudinal direction of the product at an equal distance from the long sides of the product. Longitudinal compressions are compressions arranged essentially in the longitudinal direction of the product.

The product can be provided with more than two longitudinal compressions, for example two rows of compressions arranged on each side of the center line.

According to the invention the shortest distance between the compressions can be 25–35 mm, preferably 27.5–32.5 mm. The distance between the compressions is the shortest distance between the compressions measured in the transverse direction of the product. This distance corresponds to a smaller width than the distance between the above mentioned muscle groups on both thighs of the user. The product will fold at the compressions and comfortably fit between the thighs of the user.

The shortest distance between a compression and the long side of the product which is most closely situated to the compression is suitable 5–20 mm, preferably 10–15 mm. That which is decisive for the distance between the compressions and th e long sides of the product is the function of the compressions as leakage barriers. The shortest distance between the long side of the product and the closest lying compression should be at least 5 mm, in order that it should function as a leakage barrier. The upper limit for the distance between a compression and the closest situated long side of the product is half the width of the product. If the total width of the product is small then the receiving surface for the emitted body fluid is small when the product is folded at the compressions. This leads to the risk of body fluids running off the product.

The compressions function as leakage barriers through fluid spreading preferably in the compressions. Because the pores in the compression itself during compression become smaller than the pores in the area surrounding the compression, the capacity to hold and spread fluid will be better in the compressions than in their surrounding areas. The fluid therefore preferably spreads along the compressions. The fluid will not spread across the compressions and if these are arranged as longitudinal lines in the product then they will function as leakage barriers in the transverse direction.

The length of the compressions is suitably at least 50% of the length of the absorption body. According to one embodiment the length of the compressions is 50–75% of the length of the absorption body. According to a further embodiment of the invention the length of the compressions is 60–85% of the length of the absorption body. The length of the absorption body in the product according to the invention is 200–250 mm. The absorbent product is 240–280 mm long. The different intervals of how great a part of the absorption body's length the length of the compressions forms are dependent on the absorption body and thereby the length of the product. Because the compressions are first of all intended to shape the product in order to fit against the body of the user, the length of the compressions is suitably approximately the same irrespective of the length of the absorption body. On a shorter product, with a length of 200–250 mm, the length of the compressions therefore is a great part of the length of the absorption body, such as 60–85%. On a longer product, with a length of 240–280 mm, the compressions form a smaller part of the length of the absorption body, preferably 50–75%. If the purpose of the compressions primarily is as leakage barriers, however, deviations from the above relationships can be appropriate. For example, the length of the compressions even on the longer products, 240–280 mm, can be a greater part of the length of the absorption body, such as 60–85%.

The width of the compressions, that is to say the part of the product in the transverse direction of the product which is compressed by each compression line is 1–5 mm, preferably 2–4 mm. The compressions can have the same width along the whole of their length, but the width can also vary, for example be greater in the middle of the compressions and smaller at the end parts.

The length of, and the distance between, the compressions and the bending radius of these are also dependent on the length and width of the product. For example it is suitable that with a product which is 270 mm long and 95 mm wide to have a bending radius of the compressions which is 450 mm, a distance between the compressions which is 32.5 mm and a length of the compressions which is 160 mm. When the length of the absorption body is 240 mm the compression' portion of the absorption body's length is 68%.

A product with a length which is 240 mm and a width which is 90 mm has compressions with a bending radius which is 340 mm. a distance between the compressions which is 27.5 mm and a length of the compressions which is 130 mm. When the length of the absorption body is 215 mm the length of the compressions is 60% of the length of the absorption body.

The absorbent product according to the invention can also have compressions which are united to form a coherent compression running around the product. With compressions along the whole periphery of the product leakage barriers are also obtained at the short sides of the product and possible leakage there is prevented. The distance between a compression and the closest short side of the product is suitably the same as the distance between a compression and the nearest long side of the product.

A product according to the invention has a bump situated between the compressions which fits against the vestibule of the user and encounters the body fluid eliminated by the user nearer to its outlet. The bump occurs when the compressions force up the absorption material which lies between them.

The absorbent product according to the invention is attached to the underwear of the user with the help of an adhesive region arranged on the rear side of the product. The adhesive region can for example cover the whole of the rear side of the product or can be arranged in pattern such as lines or dots. The product can also be provided with fastening tabs an arranged along the long sides of the product at the center part of the product. The attachment tabs are provided with adhesive regions on the rear side of the product. In the case when the attachment tabs are arranged on the product, the adhesive can be left off on the center part of the rear side of the product as a good attachment is anyway obtained with the help of the attachment tabs. Not having any adhesive under the center part is an advantage as the product more easily can come into contact with the body and collect fluid already where it leaves the body. During transport the adhesive regions are covered with a removable cover layer which is removed by the user when the product is to be placed in the underwear of the user. Attachment can also be mechanical, such as by press buttons or friction attachment.

The compressions are preferably made when the product is assembled. The compressions can be made for example through the product being pressed against a roller with the compression pattern on it. The compressions can be made by using just pressure or by using pressure and heat. Because the compression takes place on the whole product all the layers will be subjected to compression. Because the outer material and the rear side are thin material they will hardly be pressed together, it is the absorption layer which will be compressed. The fluid-permeable layer will be pressed down in the compressions which arise in the absorption layer.

BRIEF DESCRIPTION OF THE DRAWINGS

The invention will be described in the following in more detail with reference to the examples of embodiments which are shown on the drawings.

DETAILED DESCRIPTION OF THE INVENTION

Figure 1:
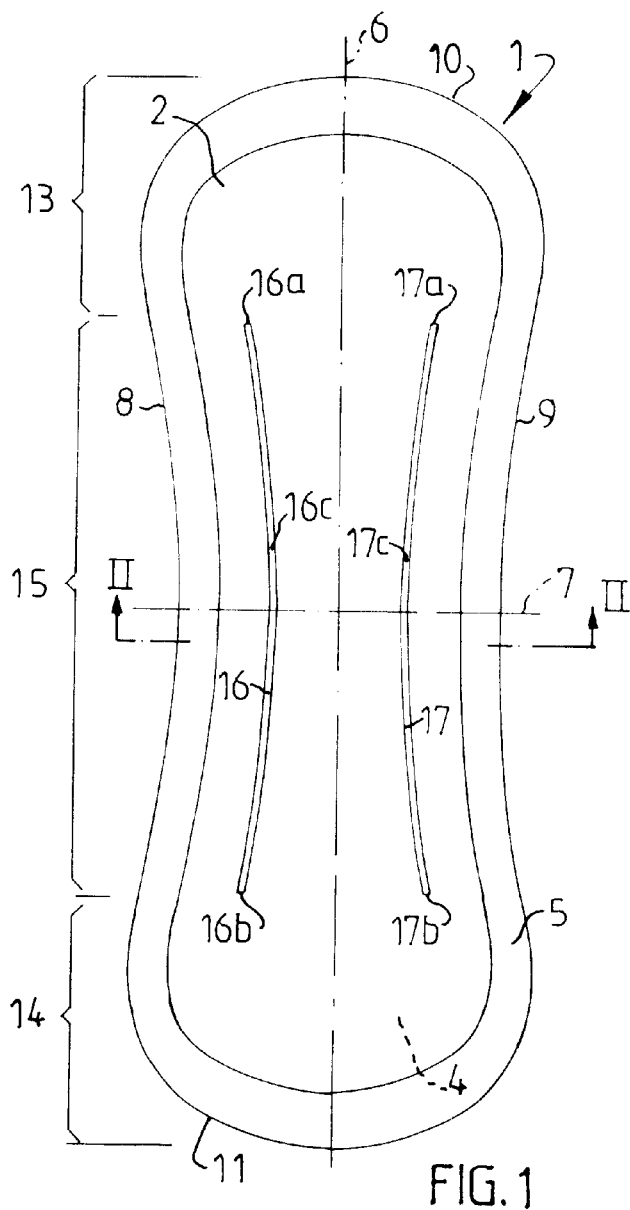
FIG. 1 shows a sanitary napkin according to the invention.
Figure 2:
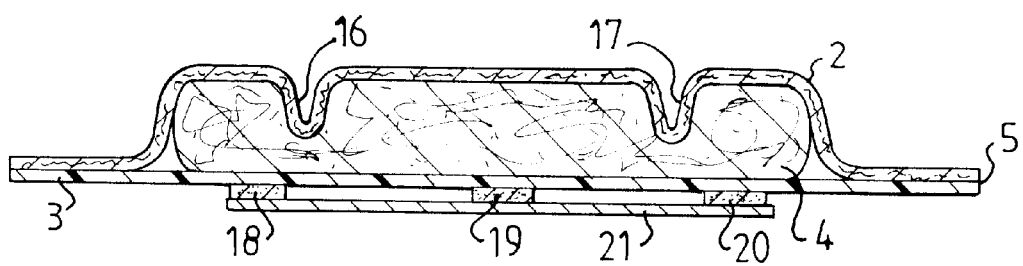
FIG. 2 shows a cross-section along line II—II in the sanitary napkin in FIG. 1.

The sanitary napkin 1 shown in FIGS. 1–2 comprises a fluid-permeable outer layer 2 arranged on the side of the sanitary napkin 1 which during use is intended to face towards the user, a fluid barrier layer 3 arranged on the side of the sanitary napkin 1 which during use is intended to face away from the user, and therebetween is positioned absorption layer 4. An alternative name for absorption layer 4 is absorption body.

The material in the outer layer 2 can, for example, be a perforated plastic film, a net of plastic or textile material, a nonwoven or a laminate made of, for example, a perforated plastic layer and a nonwoven layer. The plastic can be a thermoplastic, such as polyethene. The nonwoven material can be of natural fibres, such as cellulose or cotton wool, or synthetic fibres, such as polyethene, polypropene, polyester, polyurethane, nylon or regenerated cellulose.

The main task of the outer layer 2 in the sanitary napkin is to lead fluid into the absorption layer 4, to be soft and comfortable against the body of the user and to prevent so called rewetting, that is to say that the body fluid is forced back against the skin of the user. It is, for the sake of comfort and to prevent skin irritation, important that the surface on the part of the sanitary napkin which is in contact against the skin of the user is held as dry as possible during use. A dry surface on the sanitary napkin is experienced furthermore by the user as cooler and more comfortable during use. During changing of the sanitary napkin a dry surface is both clean and visually more attractive than a soiled, wet surface. The fluid barrier layer, or rear layer 3, consists of a fluid impermeable material. Thin, waterproof plastic films are suitable for this purpose, but it is also possible to use material which from the beginning is fluid permeable but is provided with some sort of coating of plastic, resin, or other fluid-tight material. In this way leakage of fluid from the underside of the absorbent product is prevented. The barrier layer 3 can consequently consist of any material which fulfills the criteria of fluid-impermeability and which has sufficient flexibility and skin-friendliness for the purpose. Examples of suitable material for the barrier layer are plastic films, nonwovens and laminates of these. The plastic film may, for example, be made of polyethene, polypropene or polyester. The barrier layer can alternatively consist of a laminate of a fluid impermeable plastic layer facing towards the absorption body and a nonwoven facing towards the underclothes of the user. Such a construction gives a leakage-proof barrier layer with the feel of a textile. The barrier layer can even consist of a layer of hydrophobic nonwoven or a so called SMS-laminate (spunbond-meltblown-spunbond).

The absorption layer 4 is suitably manufactured from cellulose pulp. This can exist as rolls, bales or sheets which are dry defibrated and transformed in fluffed form to a pulp web, sometimes with the mixing of so-called superabsorbents which are polymers with the ability to absorb several times their own weight of water or body fluid. Examples of other usable materials are different types of natural fibers such as cotton fibers, peat or the like. It is naturally also possible to use absorbent synthetic fibers or a mixture of natural fibers and synthetic fibers. The absorption material can further contain other components such as shape-stabilizing means, fluid spreading means or binding means such as, for example, thermoplastic fibers which have been heat-treated in order to hold the shorter fibers and particles together to form a coherent unit. It is also possible to use different types of absorbent foam material in the absorption layer.

The two outer layers 2, 3 are mutually joined outside the absorption layer 4 in a joint 5 situated along the periphery of the sanitary napkin. The sanitary napkin 1 in FIGS. 1 and 2 has an essentially elongated shape with a longitudinal direction parallel with a longitudinal center line 6 situated at equal distances from the two long sides 8, 9 of the sanitary napkin and a transverse direction parallel with a transverse center line 7 situated at equal distances from the two short sides 10 and 11 of the sanitary napkin.

The sanitary napkin 1 further has two end parts 13, 14 and a center part 15. The end parts 13, 14 each comprise approximately one quarter of the whole length of the sanitary napkin, and the center part 15 comprises approximately one half of the whole length of the sanitary napkin. This means, for example, that if the whole length of the sanitary napkin is 240 mm then the center part 15 is 120 mm long and the end parts 13, 14 are 60 mm long. The length of the sanitary napkin is 150–300 mm. The width of the sanitary napkin is 50–100 mm.

The sanitary napkins in FIGS. 1–2 has in its longitudinal direction 6 two elongated curved compressions 16, 17. The compressions 16, 17 extend in the longitudinal direction of the sanitary napkin essentially only over the center part 15 but can also extend over parts of the end parts 13, 14. The compressions 16, 17 are symmetrically arranged about the transverse center line 7. The outer ends 16a and 17a and 16b and 17b, respectively, of the curved compressions 16, 17 are at a greater distance from each other and the longitudinal center line 6 than the compressions 16, 17 are at their center parts 16c and 17c. The distances are measured in the transverse direction 7 of the sanitary napkin.

FIG. 2 shows a section along the line II—II of the sanitary napkin in FIG. 1. It can be seen here how the compressions 16, 17 have shaped the outer layer 2 and the absorption layer 4. The compression process is formed in a conventional way, for example, with the help of profiled rollers. The sanitary napkin is pressed against the profiled roller and the absorption layer 4 is compressed by the profiles of the roller. The compression process can take place with or without heating.

In FIG. 2 attachment means in the shape of strings of adhesive 18–20 are arranged on the rear side layer 3 of the sanitary napkin. The strings of adhesive 18, 19, 20 are protected before use by a cover layer 21 of release material treated paper.

Figure 3:
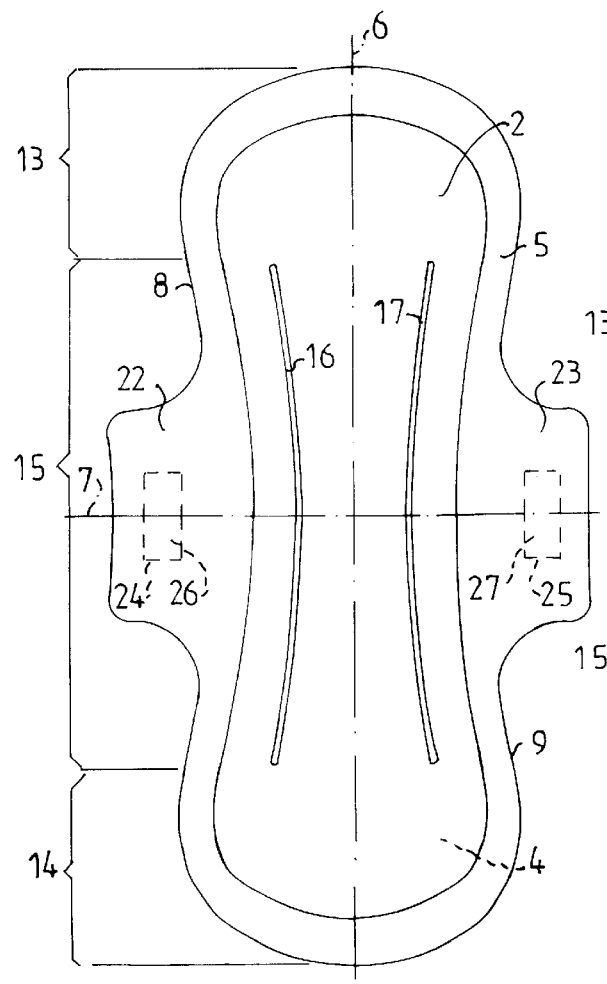
FIG. 3 shows a sanitary napkin according to an alternative embodiment of the invention.

FIG. 3 shows an alternative embodiment of the invention. The sanitary napkin in FIG. 3 has the same characteristics as the sanitary napkin in FIG. 1. In addition to this the sanitary napkin according to FIG. 3 has attachment tabs 22, 23 arranged along the long sides 8, 9 of the sanitary napkin at the center part 15 of the sanitary napkin. The attachment tabs 22, 23 are made of an extension of the outer layer 2 and the rear layer 3. They call be said to be an extension of the joint 5 which unites the outer layer 2 and the rear layer 3 outside the absorption layer 4. The outer layer 2 and the rear layer 3 are glued to each other both in the joint 5 and in the attachment tabs 22, 23. The attachment tabs can even be made in some other way, for example, formed of only the outer layer or the rear layer. They can even be made of completely separate bits of material which are attached to the sanitary napkin. On the side of the fastening tabs which are formed of the rear layer 3, that is to say the rear side, the attachment tabs are provided with adhesive regions 24, 25. The adhesive regions are covered with cover layer 26, 27 made of release agent treated paper in order to protect the adhesive regions 24, 25 until the attachment tabs 22, 23 are to be applied to the underwear of the user.

Figure 4:
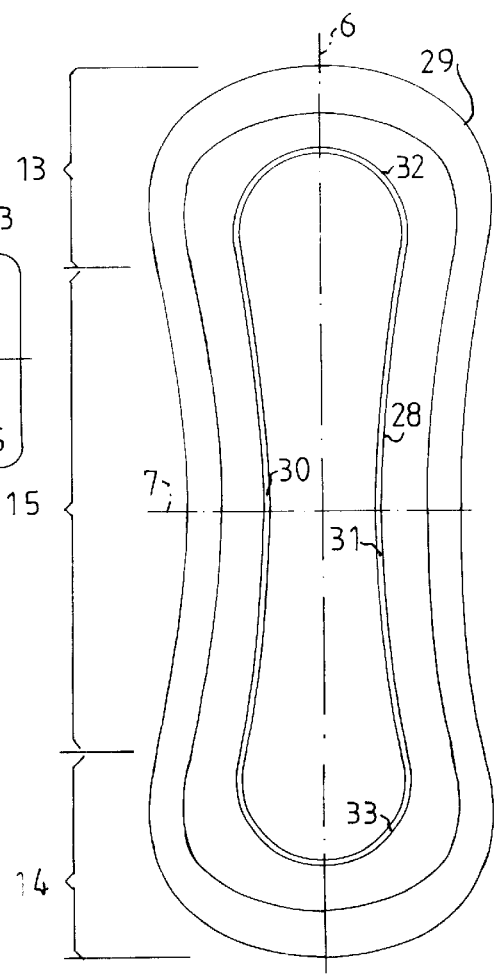
FIG. 4 shows a sanitary napkin according to a further embodiment of the invention.

FIG. 4 shows an alternative embodiment of the invention. Here a sanitary napkin which is similar to that in FIGS. 1–2 is shown but the compressions are united to form a coherent compression 28, the shape of which has the same contour as the outer contour 29 of the sanitary napkin. The compression 28 has in the center part 15 of the sanitary napkin two curved parts 30, 31 which correspond to the compressions 16, 17 of the embodiments shown according to FIGS. 1–3 and consequently lie symmetrically in relationship to the longitudinal center line 6 of the sanitary napkin and the mutual distance between them is smallest at the transverse center line 7 of the sanitary napkin and increases with increasing distance from it. In the end parts 13, 14 of the sanitary napkin the lines 30, 31 are joined by two semicircular-shaped compression parts 32, 33 to form the continuous compression 28.

We claim:

1. An absorbent product comprising:

an essentially elongated shape with a longitudinal direction and a transverse direction, two long sides, two short sides, two ends parts, a center part between the two end parts, an absorption body, and elongated, curved compressions in the longitudinal direction of the product, wherein the compressions have a bending radius of 300–450 mm.

2. The absorbent product according to claim 1, wherein the product has a longitudinal center line and the compressions are arranged on both sides of said center line so that respective end parts of said curved compressions are at a greater distance from the center line than respective center parts of said curved compressions.

3. The absorbent product according to claim 2, wherein the product has two compressions arranged one on each side of the center line.

4. The absorbent product according to claim 3, wherein the smallest distance between the compressions is 25–35 mm.

5. The absorbent product according to claim 4, wherein the smallest distance between the compressions is 27.5–32.5 mm.

6. The absorbent product according to claim 1, wherein the smallest distance between a compression and the closest of the long sides of the product is 5–20 mm.

7. The absorbent product according to claim 6, wherein the smallest distance between a compression and the closest of the long sides of the product is 10–15 mm.

8. The absorbent product according to claim 1, wherein a length of each of the compressions is at least 50% of a length of the absorption body.

9. The absorbent product according to claim 1, wherein a length of the compressions is 50–75% of a length of the absorption body.

10. The absorbent product according to claim 1, wherein a length of the compressions is 60–85% of a length of the absorption body.

11. The absorbent product according to claim 1, wherein the compressions are united to form a coherent compression running around the product.

12. The absorbent product according to claim 1, wherein the compressions have a bending radius of 320–360 mm.

* * * * *